United States Patent [19]

Paul

[11] Patent Number: 5,559,165
[45] Date of Patent: Sep. 24, 1996

[54] HOT MELT ADHESIVES FOR BONDING TO SENSITIVE AREAS OF THE HUMAN BODY

[75] Inventor: Charles W. Paul, Madison, N.J.

[73] Assignee: National Starch and Chemical Investment Holding Corporation, Wilmington, Del.

[21] Appl. No.: 512,579

[22] Filed: Aug. 8, 1995

[51] Int. Cl.[6] .......................... C08L 93/04; C08L 57/02; C08L 53/02; C08K 5/01

[52] U.S. Cl. .......................... 523/111; 524/271; 524/274; 524/499; 524/505; 524/474; 524/490; 525/88; 525/89; 525/95; 525/98; 525/99; 525/92

[58] Field of Search .......................... 523/111; 524/271, 524/274, 505, 499, 474, 490; 525/88, 89, 95, 98, 99, 92

[56] References Cited

U.S. PATENT DOCUMENTS

| | | | |
|---|---|---|---|
| T100,203 | 1/1981 | Lauck | 524/505 |
| 3,917,607 | 11/1975 | Crossland et al. | 524/478 |
| 3,954,692 | 5/1976 | Downey | 524/271 |
| 4,259,220 | 3/1981 | Bunelle et al. | 525/98 |
| 4,369,284 | 1/1983 | Chen | 524/476 |
| 4,399,249 | 8/1983 | Bildusas | 524/271 |
| 4,418,123 | 11/1983 | Bunelle et al. | 428/517 |
| 4,543,099 | 9/1985 | Bunelle et al. | 604/385 |
| 4,757,114 | 7/1988 | Tochinai et al. | 524/499 |
| 4,761,341 | 8/1988 | Rosiak et al. | 428/512 |
| 4,785,043 | 11/1988 | Kawai et al. | 524/274 |
| 4,822,653 | 4/1989 | Kauffman et al. | 428/34.2 |
| 4,833,193 | 5/1989 | Sieverding | 524/505 |
| 4,900,770 | 2/1990 | Tomita et al. | 524/274 |
| 5,001,179 | 3/1991 | Kauffman et al. | 524/275 |
| 5,149,741 | 9/1992 | Alper et al. | 524/271 |
| 5,262,468 | 11/1993 | Chen | 524/476 |
| 5,290,842 | 3/1994 | Sasaki et al. | 524/505 |
| 5,331,038 | 7/1994 | Dillman | 525/98 |
| 5,360,350 | 11/1994 | Koblitz et al. | 525/89 |
| 5,459,193 | 10/1995 | Anderson et al. | 525/98 |

FOREIGN PATENT DOCUMENTS

| | | | |
|---|---|---|---|
| 0175562 | 9/1985 | European Pat. Off. | C09J 3/14 |
| 2539412 | 3/1976 | Germany | 524/274 |
| 0072047 | 6/1978 | Japan | 524/499 |
| 0226578 | 11/1985 | Japan | 524/505 |
| 0202572 | 8/1990 | Japan | 524/499 |
| 0013935 | 9/1991 | WIPO | 524/505 |

OTHER PUBLICATIONS

Overview entitled "Hydrogen Skin Adhesives", by James J. Perrault, Operations Manager, Promeon Medical Division, Medtronic, Inc., pp. 78–83.

*Primary Examiner*—Peter A. Szekely
*Attorney, Agent, or Firm*—Ellen T. Dec

[57] ABSTRACT

A pressure sensitive hot melt adhesive comprising a block copolymer and 60 to 95 parts of a liquid diluent, the adhesive being characterized by a midblock Tg less than −10° C., a G' less than $15 \times 10^4$ dynes/cm$^2$ at 10 rad/s, 25° C., a G" of 1 to $6 \times 10^4$ dynes/cm$^2$ and a tensile strength greater than 10 psi exhibit superior properties, without the need for any curing operation after cooling.

20 Claims, No Drawings

HOT MELT ADHESIVES FOR BONDING TO SENSITIVE AREAS OF THE HUMAN BODY

BACKGROUND OF THE INVENTION

This invention relates to the use of hot melt pressure-sensitive adhesives which adhere well to the human skin and hair, and are therefore useful for a variety of medical and other products.

Although many adhesive compositions are known, very few of these are completely satisfactory for application to human skin. The requirements for such adhesives are stringent; they must adhere well to human skin during perspiration, when the weather is hot, or in an environment of draining wounds, yet be removable without leaving adhesive residue on the skin's surface. Moreover, adhesion should take effect immediately on application to skin, even in a hot or moist environment, and should release cleanly and with minimal discomfort when voluntarily removed in this environment.

Adhesives applied to sensitive areas of the human body require further special characteristics. Hair covered regions are especially difficult to adhere well to without causing pain upon removal of the adhered article. For such regions, a soft adhesive with minimal viscoelastic loss is required. Hydrogels have been used effectively for such purposes, but have their own disadvantages, including high price, special packaging and release layers to retain the moisture (typically about 40% of the total adhesive), as well as variations in properties during use in response to changes in humidity. Other disadvantages arise from the general necessity of a non-woven support to strengthen the adhesive and hold it in place during cure. Once cured, a water impervious release layer is applied.

To obtain a soft adhesive while maintaining solid-like behavior requires high molecular weight polymers be used. With hydrogels this is obtained by crosslinking or curing after cooling, as is the case with an electron beam curable acrylic described in European Patent Application EP 175562 A2. Further, U.S. Pat. No. 5,262,468 to Chen describes the use of very high molecular weight rubbers to obtain gelatinous thermoplastic compositions, but such compositions generally lack in adhesive grab so that virtually no adhesion to the body is obtained.

It is an object of the present invention to obtain an adhesive with the desirable characteristics of a hydrogel, but without the drawbacks. In particular, a hot melt adhesive has been discovered that requires no subsequent cure, but functions like a hydrogel.

SUMMARY OF THE INVENTION

Hot melt pressure sensitive adhesives especially suited for adhesive skin application comprise at least one block copolymer and a liquid diluent, the adhesive being characterized by a midblock Tg of less than $-10°$ C., a G' (storage modulus) less than $15 \times 10^4$ dynes/cm$^2$ at 10 rad/s. ($25°$ C.), generally at least $1 \times 10^4$ and preferably 4 to $10 \times 10^4$ dynes/cm$^2$; a G" (loss modulus of 1 to $6 \times 10^4$ dynes/cm$^2$ and a tensile strength greater than 10 psi exhibit superior properties, these properties being obtained without the need for any curing operation after cooling.

In particular, suitable hot melt pressure sensitive adhesives comprise 1 to 20 parts of a high molecular weight rubber triblock or radial block copolymer; 0 to 20 parts high molecular weight diblock rubber, 0 to 10 parts by weight of other compatible high molecular weight polymers; 0 to 30 parts by weight end block resin; 60 to 95 parts by weight oil or other liquid midblock diluent; 0 to 50 parts by weight of a solid tackifier which is compatible with the polymer midblock and 0 to 3 parts by weight anti-oxidant; the parts to total 100 parts by weight.

DETAILED DESCRIPTION OF THE PREFERRED EMBODIMENTS

It will be understood by those skilled in the art that there are a variety of ways to formulate the particular raw materials in order to obtain an adhesive having the desired midblock Tg, G' and G" values. Moreover, the particular end use for which the adhesive is intended will also affect the choice of materials and the ultimate G' and G" values. It is however, possible to generally define the raw materials which may be utilized and to characterize what properties will be provided by the use of the various materials.

As used herein the term "high molecular weight rubbers" are those with a viscosity at $25°$ C. of above 1,000 cP in toluene at a concentration of 20% by weight.

In the case of the high viscosity triblock copolymers employed herein, they may have the more general configuration A-B-A wherein the polymer blocks A are non-elastomeric polymer blocks which, as homopolymers have glass transition temperatures above $20°$ C., while the elastomeric polymer blocks B are isoprene, or butadiene which may be partially or substantially hydrogenated or mixtures thereof. Further, the copolymers may be linear or branched. Typical branched structures contain an elastomeric portion with at least three branches which can radiate out from a central hub or can be otherwise coupled together.

The non-elastomeric blocks may comprise homopolymers or copolymers of vinyl monomers such as vinyl arenes, vinyl pyridines, vinyl halides and vinyl carboxylates, as well as acrylic monomers such as acrylonitrile, methacrylonitrile, esters of acrylic acids, etc. Monovinyl aromatic hydrocarbons include particularly those of the benzene series such as styrene, vinyl toluene, vinyl xylene, ethyl vinyl benzene as well as dicyclic monovinyl compounds such as vinyl naphthalene and the like. Other non-elastomeric polymer blocks may be derived from alpha olefins, alkylene oxides, acetals, urethanes, etc. Styrene is preferred.

The elastomeric block component making up the remainder of the copolymer is isoprene or butadiene which may be hydrogenated as taught, for example, in U.S. Pat. No. 3,700,633. This hydrogenation of butadiene may be either partially or substantially complete. Selected conditions may be employed for example to hydrogenate the elastomeric butadiene block while not so modifying the vinyl arene polymer blocks. Other conditions may be chosen to hydrogenate substantially uniformly along the polymer chain, both the elastomeric and non-elastomeric blocks thereof being hydrogenated to practically the same extent, which may be either partial or substantially complete. Hydrogenated polymers are preferred to minimize degradation during processing, which is a more severe problem with higher molecular weight polymers.

The high viscosity triblock copolymer of the invention can have a broad range of non-elastomeric end block to elastomeric center block ratio of approximately about 5:95 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C. Although the typical ratio values for Kraton G 1651, 4600, and 4609 are approximately about 33:67 and for Kraton G 1855X approximately about 27:73, as noted previously, these ratios can vary broadly from the typical product specification values.

It is preferred that the adhesive additionally contain 1 to 20, preferably 3 to 8, parts by weight of a high molecular weight (i.e., viscosity>1000 cps at 25° C. at 20% in toluene) diblock polymer of the general A–B configuration where A and B are as described previously. Preferred are Kraton G 1701X or 1702X which are both styrene ethylene propylene diblock polymers. Kraton G1702X is most preferred.

While it is preferred the formulation contain some diblock polymer, the diblock may be replaced entirely or in part with another high molecular weight polymer that is compatible with the system. For example, polyisobutylene (e.g., Vistanex from Exxon), polyisoprene (e.g., from Kuraray), or styrene/butadiene copolymer (e.g., Pliofiex from Goodyear) may be used in amounts of about 2 to 10 parts by weight.

As will be described hereinbelow, various additives are known to associate with the particular blocks (domains) of the block polymer(s), altering the behavior of those portions accordingly. In more detail, the mid-block portion or domain (i.e., the "B-block") of the polymer generally has a very low Tg (e.g., on the order of about −50° C.). As other mid-block compatible components such as plasticizing oils and tackifiers are added, these components associate with the B domains swelling them and generally resulting in a change in the Tg thereof. For most pressure sensitive adhesive applications, a Tg in the range of about 0° C. to 25° C., preferably about 15° C. is desirable; however, for use herein mid-block Tg ranges of less than about −10° C. are required.

Thus, there is also present in the adhesive about 60 to 95 parts by weight, preferably 70 to 80 parts, of an oil or other liquid diluent which is primarily aliphatic in character and is compatible with the polymer midblock. Included in these materials are plasticizers such as paraffinic and naphthenic petroleum oils, highly refined aromatic-free paraffinic and naphthenic food and technical grade white petroleum mineral oils, and liquid tackifiers such as the synthetic liquid oligomers of polybutene, polypropene, polyterpene, etc. The synthetic series process oils are high viscosity oligomers which are permanently fluid liquid monolefins, isoparaffins or paraffins of moderate to high molecular weight. Liquid plasticizing or tackifying diluents include polyterpenes such as Wingtack 10 available from Goodyear, and Escorez 2520 based on a C5 feed stream available from Exxon Chemical. Other liquid diluents would include polyisoprene, available as LIR 50 from Kuraray, Amoco's polybutenes available under the name Indopol. Most preferred are paraffinic oils in combination with Escorez 2520, a polymerized $C_5$ petroleum feed stream.

There may also be present up to 50 parts, preferably 10 to 20 parts by weight of a solid tackifier (i.e., one having a Ring and Ball softening point above 25° C.) which is compatible with the midblock. Suitable tackifiers include any compatible resins or mixtures thereof such as (1) natural or modified rosins such, for example, as gum rosin, wood rosin, tall-oil rosin, distilled rosin, hydrogenated rosin, dimerized rosin, and polymerized rosin; (2) glycerol and pentaerythritol esters of natural or modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, e.g., styrene/terpene and alpha methyl styrene/terpene; (4) polyterpene resins having a softening point, as determined by ASTM method E28,58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof, for example, as the resin product resulting from the condensation, in an acidic medium, of a bicyclic terpene and phenol; (6) aliphatic petroleum hydrocarbon resins having a Ball and Ring softening point of from about 70° to 135° C.; the latter resins resulting from the polymerization of monomers consisting of primarily of olefins and diolefins; also included are the hydrogenated aliphatic petroleum hydrocarbon resins; (7) alicyclic petroleum hydrocarbon resins and the hydrogenated derivatives thereof; and (8) aliphatic/aromatic or cycloaliphatic/aromatic copolymers and their hydrogenated derivatives.

Preferred tackifiers for use herein include polyterpenes such as Wingtack 95 from Goodyear; aliphatic resins such as Hercures C from Hercules; cycloaliphatic resins such as Eastotac H100 from Eastman; and aliphatic/aromatic or cycloaliphatic/aromatic resins such as ECR 149B or ECR 179A from Exxon Chemical. Most preferred are the aliphatic or cycloaliphatic resins while the least desirable are the rosin esters or phenolic modified polyterpenes are least preferred.

The desirability and selection of the particular tackifying agent is, in large part, dependent upon the specific block copolymer employed.

Additionally, it may be desirable to incorporate in the adhesive up to 30 parts by weight of an end block resin. End block resins are those resins which reside predominantly in the non-elastomer domains of the rubber after the adhesive is cooled. Representative of such resins are the primarily aromatic resins based on mixed C9 petroleum distillation streams such as the Hecures materials available from Hercules, or resins based on pure or mixed monomer streams of aromatic monomers such as homo or copolymers of vinyl toluene, styrene, alpha-methyl styrene, coumarone or indene. Preferred are those based on alpha-methyl styrene available from Hercules under the Kristalex trade name. If present, the end block resin is generally used in an amount of 5 to 30 parts by weight, preferably less than 20 parts.

Optionally there may also be present 0 to 5% by weight of a wax component such as the polyethylene waxes available from Allied-Signal under the A–C symbol. If used, the wax is generally present in an amount of at least 2 parts by weight.

Finally, antioxidants typically used in the production of rubber based pressure sensitive adhesives may be present in an amount up to about 3 parts by weight. Among the applicable stabilizers or antioxidants utilized herein are included high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group hereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4- hydroxybenzyl) benzene; pentaerythrityl tetrakis-3(3,5-di-tert-butyl-4-hydroxyphenyl)-propionate; 4,4'-methylenebis (2,6-tert-butylphenol); 4,4'-thiobis (6-tert-butyl-o-cresol); 2,6-di-tert-butylphenol; 6-(4-hydroxyphenoxy)-2,4-bis(n-octylthio)-1,2,5-triazine; di-n-octadecyl3,5-di-tert-butyl-4-hydroxybenzyl phosphonate; 2-(n-octylthio)ethyl 3,5-di-tert-butyl-4-hydroxybenzoate; and sorbitol hexa[3-(3,5-di-tert-butyl-4-hydroxyphenyl)-propionate].

As was noted above, there are a variety of ways to formulate the particular raw materials in order to obtain an adhesive having the desired midblock Tg, G' and G" values. Moreover, the particular end use for which the adhesive is intended will also affect the choice of materials and the ultimate Tg, G' and G" values. In general, it has been found that the triblock rubber provides the set of the adhesive into a gelatinous solid, while the diblock rubber improves the tack of the formulation, as does the liquid resin. The substitution of liquid resin for oil also inhibits bleed into the release paper against which the adhesive is stored. The end block resin also provides strength to the adhesive formulation while lowering its melt viscosity by reducing the self-association of the rubber end blocks when molten. In formulating the adhesives, predominately liquid diluents are used to ensure a low Tg for the matrix (midblock portion) of the formulation. A low Tg leads to fast polymer relaxation times which in turn lead to low pain upon removal of the adhesive.

Using the above parameters as guidelines, we have found that particularly preferred adhesives may be prepared from about 10 parts of polymer, equally split between triblock and diblock, preferably Kraton G 1651 and Kraton G1702, respectively. These rubbers are used in combination with 5 to 30 parts, preferably 10–20 parts of end block resin, with Kristalex α-methyl styrene resins most preferred. The remainder of the product is diluent and tackifier. The lower the blend Tg of the remainder, the less tack and lower peel the adhesive will exhibit. Preferably the remainder is liquid diluent, either oil or a blend of oil and liquid tackifier. Most preferred is about a 50/50 blend of a paraffin oil (such as Kaydol available from Witco) and liquid tackifier. The most preferred liquid tackifier is Escorez 2520, a polymerized $C_5$ petroleum feed stream which has a Tg of $-16°$ C. A particularly preferred hot melt adhesive composition comprises 3 to 8 parts of the triblock polymer, 3 to 8 parts diblock, 5 to 30 parts end block resin, the remainder (to 100 parts) comprising a liquid diluent, a liquid tackifier and optionally a solid tackifier such that the blend of the diluent and tackifier(s) exhibits a Ring and Ball softening point below 25° C.

Additional guidance for formulating adhesives having a wide range of properties may be obtained from the examples which follow.

The resultant hot melt adhesives are useful as ostomy seals, adhesive tapes and bandages, wound drainage adhesive seals, wound dressings, as adherents for other products and the like that adhere to human skin and remain adherent even in a moist environment.

In the examples which follow, unless otherwise specified, all parts are by weight and all temperatures in degree Celsius.

All viscosities were measured using a Brookfield viscometer with a #27 spindle.

EXAMPLE

All the formulations described herein were prepared in a 600 g Brabender mixer with sigma blades. The rubbers and about half the oil in the formulation were added to the bowl preheated to about 325° F. Once homogenous, additional oil was added and any other liquid diluents. Finally the end block tackifier was added. The formulations are shown in Table 1 while the properties thereof are in Table 3. For comparative purposes, two commercially used materials were also evaluated. Thus, Example 8 illustrates the use of MQ 7965, a hot melt adhesive commercially used for body plasters and available from Kanebo/NSC while Example 9 shows the use of a Promeon hydrogel.

TEST PROCEDURES

A Rheometrics Dynamic Mechanical Analyzer (Model RDA 700) was used to obtain the elastic (G') and loss (G") moduli versus temperature. The instrument was controlled by Rhios software version 4.3.2. Parallel plates 8 mm in diameter and separated by a gap of about 2 mm were used. The sample was loaded and then cooled to about $-100°$ C. and the time program started. The program test increased the temperature at 5° C. intervals followed by a soak time at each temperature of 10 seconds. The convection oven containing the sample was flushed continuously with nitrogen. The frequency was maintained at 10 rad/s. The initial strain at the start of the test was 0.05% (at the outer edge of the plates). An autostrain option in the software was used to maintain an accurately measurable torque throughout the test. The option was configured such that the maximum applied strain allowed by the software was 80%. The autostrain program adjusted the strain at each temperature increment if warranted using the following procedure. If the torque was below 200 g-cm the strain was increased by 25% of the current value. If the torque was above 1200 g-cm it was decreased by 25% of the current value. At torques between 200 and 1200 g-cm no change in strain was made at that temperature increment. The shear storage or elastic modulus (G') and the shear loss modulus (G") are calculated by the software from the torque and strain data. Their ratio, G"/G', also known as the tan delta, was also calculated.

The mid block Tg was taken as the maximum in tan delta.

Tensile strength was determined on 0.125" thick, 2.5" long dogbone shaped portions with 1"×1" end tabs and a 0.5"×0.5" central gage portion. These were pulled on an Instron with pneumatic grips at a speed of 20"/min. Strength was taken as the maximum stress during the test.

Skin adhesion was assessed by applying a film of adhesive on a backing to the forearm and removing slowly (about 1"/sec).

TABLE 1

ADHESIVE FORMULATIONS

| | EXAMPLE | | | | | | |
|---|---|---|---|---|---|---|---|
| | 1 | 2 | 3 | 4 | 5 | 6 | 7 |
| Kraton | | | | | | | |
| G 1651 | 10 | — | 10 | 5 | 5 | 5 | — |
| G 1657 | — | 20 | — | — | — | — | — |
| G 1654 | — | — | — | — | — | — | 8 |
| G 1702 | — | — | — | 5 | 5 | 5 | 8 |
| Mineral Oil (Kaydol) | 90 | 80 | 80 | 80 | 40 | 40 | 74 |
| Wingtack 10 | — | — | — | — | 20 | — | — |
| Escorez 2520 | — | — | — | — | — | 40 | — |
| Kristalex 3085 | — | — | 10 | 15 | 15 | 15 | 15 |
| Viscosity at 325° F. | >500,000 | 3,925 | 31,700 | 14,300 | 2,910 | 640 | 21,300 |

Wingtack 10 is a synthetic polyterpene from Goodyear Chemicals.
Escorez 2520 is a liquid hydrocarbon resin available from Exxon Chemical Co.
Kristalex 3085 is an alpha-methyl styrene tackifying resin with a softening point of 85° C. available from Hercules.

TABLE 2

RUBBER[a] CHARACTERISTICS

| Sample | Viscosity (Cp) | % Styrene by Weight | % Diblock |
|---|---|---|---|
| Kraton G 1651 | 5560[b] | 33 | 0 |
| Kraton G 1657 | 1365[c] | 13 | 35 |
| Kraton G 1702 | 3180[b] | 28 | 100 |
| Kraton G 1654 | 111,500[c] | 31 | 0 |

[a]Kraton rubbers obtained from Shell Chemical Company
[b]Viscosity at 25° C. in toluene at a polymer concentration of 10%
[c]Viscosity at 25° C. in toluene at a polymer concentration of 20%

Example 2 employs higher levels of a lower molecular weight rubber containing substantial diblock. The adhesive was clear and homogeneous, but much too stiff (high G') and lacking in tack and therefore not suitable for use herein. Conformablity over hair-covered surfaces is inadequate at such a high level of stiffness.

Example 3 incorporates an end block resin to add strength and lower viscosity. The resultant adhesive was clear and homogeneous, but had insufficient tack and hold due to low G" ($<10^4$ dynes/cm$^2$).

Example 4 demonstrates the present invention in its simplest form. Thus, the composition of this Example is formulated so as not to appreciably change the very low Tg of the polymer midblock while providing the proper rheological properties, i.e., a G' value less than $15 \times 10^4$ dynes/cm$^2$ and a G" value within the range of 1 to $6 \times 10^4$ dynes/cm$^2$.

Example 5 demonstrates how increasing the polymer concentration and replacing part of the oil with a liquid resin increases the stiffness and tack of the adhesive.

Example 6 contrasts with Example 4 to demonstrate how liquid resin (replacing oil) can be used to reduce the adhesive viscosity while increasing tack and peel.

Example 7 demonstrates that increasing the rubber concentration increases the stiffness of the product therefore reducing the grab.

Example 8 demonstrates that a commercially available A-B-A block polymer based adhesive for skin contact (MQ 7965 from Kanebo/NSC) is unacceptably aggressive on skin; while Example 9 describes the properties of a 25 mil thick film of a hydrogel obtained from Promeon Medical (RG-63B 25H5). In the latter case, grab was good with minimal pain upon removal.

TABLE 3

ADHESIVE PROPERTIES

| Example | G' ($10^4$ dynes/cm$^2$) 25° C. | G" ($10^4$ dynes/cm$^2$) 25° C. | Tan Delta 25° C. | Tg (°C.) | Tensile Strength (psi) | Loop Tack[a] on Steel (oz/in$^2$) | 180° Peel off of HDPE[c] (lb/in) | Skin Grab | Adhesive[b] Removal (Pain) |
|---|---|---|---|---|---|---|---|---|---|
| 1 | 4.32 | 0.56 | 0.129 | −57 | — | 0 | 0.03 | poor | none |
| 2 | 51.3 | 11.7 | 0.227 | −47 | — | 9 | 0.11 | fair | none |
| 3 | 6.43 | 0.91 | 0.142 | −53 | — | 2 | 0.03 | good | none |
| 4 | 2.90 | 1.62 | 0.562 | −50 | 18 | 8 | 0.07 | good | none |
| 5 | 6.87 | 3.20 | 0.468 | −40 | 25 | 15 | 0.15 | excellent | none |
| 6 | 6.60 | 2.19 | 0.333 | −20 | 26 | 20 | 0.32 | excellent | none |
| 7 | 13.4 | 4.85 | 0.343 | −53 | — | 8 | 0.05 | fair | none |
| 8 (C) | 16.7 | 7.00 | 0.417 | −32 | — | 25 | 0.24 | excellent | moderate |
| 9 (C) | 9.22 | 5.04 | 0.546 | −60 | — | — | — | good | slight |

[a]2 mil films backed with 1.5 mil Mylar
[b]2 mil films with 1.5 mil Mylar except for Example 9 (Hydrogel) which was applied as a 25 mil with no backing
[c]high density polyethylene plates, 1/8" thick Example 1 demonstrates a formulation as described in U.S. Pat. No. 4,369,284 to J. Chen. This formula exhibits the desired softness (G' at 25° C.$<15 \times 10^4$ dynes/cm$^2$), but has insufficient grab due to low loss modulus (G" at 25° C.$<1 \times 10^4$ dynes/cm$^2$) and is therefore not suitable for the adhesive applications described herein.

TABLE 4

ADHESIVE FORMULATIONS

| | EXAMPLE | | | | | | |
|---|---|---|---|---|---|---|---|
| | 10 | 11 | 12 | 13 | 14 | 15 | 16 |
| Kraton | | | | | | | |
| G 1651 | 5 | 5 | 5 | 5 | 5 | 5 | 5 |
| G 1702 | 5 | 5 | 5 | 5 | 6 | 8 | 10 |
| Mineral Oil (Kaydol) | 35 | 35 | 30 | 40 | 40 | 40 | 40 |
| Escorez 2520 | 40 | 40 | 50 | 40 | 39 | 37 | 35 |
| Kristalex 3085 | 15 | 15 | 15 | — | 15 | 15 | 15 |
| AC 400 | 5 | — | — | — | — | — | — |
| AC 617 | — | 5 | — | — | — | — | — |
| Viscosity at 325° F. | 2100 | 2238 | 1000 | 3763 | 1475 | 3950 | 11,350 |

AC 400 is an ethylene vinyl acetate wax from Allied-Signal.
AC 617 is a polyethylene wax from Allied-Signal.

TABLE 5

ADHESIVE PROPERTIES

| Example | G' ($10^4$ dynes/cm$^2$) | G" ($10^4$ dynes/cm$^2$) | Tan Delta | Mid-block Tg (°C.) | Tensile Strength (psi) | Loop Tack[a] on Steel (oz/in$^2$) | 180° Peel off of HDPE[c] (lb/in) | Skin Grab | Adhesive[b] Removal (Pain) |
|---|---|---|---|---|---|---|---|---|---|
| 10 | 12.10 | 3.32 | 0.271 | −17 | — | 22 | 0.13 | good | minimal |
| 11 | 17.66 | 4.58 | 0.260 | −20 | — | 14 | 0.11 | good | slight |
| 12 | 7.58 | 2.48 | 0.327 | −12 | 38 | 28 | 0.36 | — | — |
| 13 | 8.14 | 2.45 | 0.302 | −34 | — | 9 | 0.10 | good | none |
| 14 | 8.86 | 2.42 | 0.272 | −24 | — | 17 | 0.17 | excellent | none |
| 15 | 12.06 | 3.35 | 0.278 | −24 | — | 15 | 0.27 | v. good | none |
| 16 | 13.17 | 3.49 | 0.265 | −27 | — | 15 | 0.25 | good | none |

[a] 2 mil films backed with 1.5 mil Mylar
[b] 2 mil films backed with 1.5 mil Mylar
[c] high density polyethylene plates, 1/8" thick Example 10 has part of the mineral oil replaced by a wax to create a product with a drier, slightly stiffer feel and appearance suitable for some applications while the results of Example 11 show that the use of the same amount of a different wax yields excess stiffness (G') rendering the adhesive unsuitable for these applications.

Example 12 is a modification of Example 6 wherein part of the mineral oil is replaced by additional liquid resin, thereby increasing the stiffness (G'), tack, and mid-block Tg.

Example 13 demonstrates a formula containing no end block resin.

Examples 14–16 show that increasing the level of diblock (relative to Example 6) increases both G' and G", while also increasing the viscosity.

I claim:

1. A pressure sensitive hot melt adhesive comprising a high molecular weight block copolymer and 60 to 95 parts by weight oil or other liquid midblock diluent, the adhesive being characterized by a midblock Tg less than −10° C., a G' less than 15×10$^4$ dynes/cm$^2$ at 10 rad/s (25° C.), a G" of 1 to 6×10$^4$ dynes/cm$^2$ (25° C.) and a tensile strength greater than 10 psi and requiring no subsequent curing operation after cooling.

2. A hot melt pressure sensitive adhesive comprising 1 to 20 parts of an A-B-A rubber triblock or radial block copolymer having a viscosity at 25° C. of above 1,000 cP in toluene at a concentration of 20% by weight wherein the polymer blocks A are non-elastomeric polymer blocks which, as homopolymers have glass transition temperatures above 20° C., while the elastomeric polymer blocks B are isoprene, or butadiene which may be partially or substantial hydrogenated or mixtures thereof; 0 to 20 parts A–B diblock rubber having a viscosity at 25° C. of above 1,000 cP in toluene at a concentration of 20% by weight; 0 to 10 parts by weight of another compatible high molecular weight polymer having a viscosity at 25° C. of above 1,000 cP in toluene at a concentration of 20% by weight; 0 to 30 parts by weight end block resin; 60 to 95 parts by weight oil or other liquid midblock diluent; 0 to 40 parts by weight of a solid tackifier which is compatible with the polymer midblock; 0 to 5 parts wax, and 0 to 3 parts by weight anti-oxidant; the parts to total 100 parts by weight; the adhesive also characterized by a midblock Tg less than −10° C., a G' less than 15×10$^4$ dynes/cm$^2$ at 10 rad/s (25° C.), a G" of 1 to 6× 10$^4$ dynes/cm$^2$ (25° C.) and a tensile strength greater than 10 psi and requiring no subsequent curing operation after cooling.

3. The hot melt adhesive of claim 2 wherein A in the rubbery triblock and diblock polymer is styrene and B is isoprene or butadiene or the hydrogenated derivatives thereof.

4. The hot melt adhesive of claim 2 wherein the triblock copolymer has a range of non-elastomeric end block to elastomeric center block ratio of 5:95 to 40:60.

5. The hot melt adhesive of claim 2 wherein the triblock copolymer is styrene-ethylene-butylene-styrene.

6. The hot melt adhesive of claim 2 containing 1 to 20 parts by weight of an A-B diblock polymer.

7. The hot melt adhesive of claim 6 wherein the diblock copolymer is a styrene ethylene propylene diblock polymer.

8. The hot melt adhesive of claim 2 containing 2 to 10 parts by weight of a high molecular weight polymer having a viscosity at 25° C. of above 1,000 cP in toluene at a concentration of 20% by weight that is compatible with the system.

9. The hot melt adhesive of claim 8 wherein the high molecular weight polymer is polyisobutylene, polyisoprene, or styrene/butadiene copolymer.

10. The hot melt adhesive of claim 2 containing 5 to 30 parts by weight of an end block resin.

11. The hot melt adhesive of claim 10 wherein the end block resin is a primarily aromatic resin based on mixed C9 petroleum distillation streams.

12. The hot melt adhesive of claim 10 wherein the end block resin is a homo or copolymer of vinyl toluene, styrene, alpha-methyl styrene, coumarone or indene.

13. The hot melt adhesive of claim 2 containing 60 to 95 parts by weight of an oil or other liquid diluent which is primarily aliphatic in character and is compatible with the polymer midblock.

14. The hot melt adhesive of claim 13 wherein the liquid diluent is selected from the group consisting of paraffinic and naphthenic petroleum oils, highly refined aromatic-free paraffinic and naphthenic food and technical grade white petroleum mineral oils, synthetic liquid oligomers of polymerized $C_5$ petroleum feed stream, polybutene, polypropene, polyterpene, polyterpenes, polyisoprene, and polybutene.

15. The hot melt adhesive of claim 2 containing 10 to 50 parts by weight of a solid tackifier selected from the group consisting of (1) natural or modified rosins, (2) glycerol and pentaerythritol esters of natural or modified rosins, (3) copolymers and terpolymers of natural terpenes, (4) polyterpene resins having a softening point, as determined by ASTM method E28,58T, of from about 80° to 150° C., (5) phenolic modified terpene resins and hydrogenated derivatives thereof, (6) aliphatic petroleum hydrocarbon resins having a Ball and Ring softening point of from about 70° to 135° C., and (7) alicyclic petroleum hydrocarbon resins and the hydrogenated derivatives thereof; and (8) aliphatic/aromatic or cycloaliphatic/aromatic copolymers and their hydrogenated derivatives.

16. The hot melt adhesive of claim 15 wherein the tackifier is a polyterpene, an aliphatic resin, a cycloaliphatic resin, or an aliphatic/aromatic or cycloaliphatic/aromatic resin.

17. The hot melt adhesive of claim 16 wherein the tackifier is an aliphatic or cycloaliphatic resin.

18. The hot melt adhesive of claim 2 containing 2 to 5% by weight of a wax.

19. A hot melt adhesive composition of claim 2 comprising 3 to 8 parts of the triblock polymer, 3 to 8 parts diblock, 5 to 30 parts end block resin, the remainder (to 100 parts) comprising a liquid diluent, and a liquid tackifier such that the blend of the diluent and tackifier exhibits a Ring and Ball softening point below 25° C.

20. The hot melt adhesive of claim 19 wherein the diluent additionally contains 10 to 50 parts by weight of a solid tackifier.

* * * * *